United States Patent
Agarwal et al.

(10) Patent No.: US 9,783,492 B2
(45) Date of Patent: Oct. 10, 2017

(54) PROCESS FOR THE PREPARATION OF FLUVOXAMINE MALEATE

(71) Applicant: ZCL CHEMICALS LIMITED, Mumbai (IN)

(72) Inventors: Nand Lal Agarwal, Bharuch (IN); Trushar Dahyabhai Patel, Bharuch (IN); Pintu Balubhai Loriya, Bharuch (IN)

(73) Assignee: ZCL CHEMICALS LIMITED, Munbai, Maharashtra (IN)

( * ) Notice: Subject to any disclaimer, the term of this patent is extended or adjusted under 35 U.S.C. 154(b) by 25 days.

(21) Appl. No.: 14/436,515

(22) PCT Filed: Mar. 26, 2014

(86) PCT No.: PCT/IN2014/000192
§ 371 (c)(1),
(2) Date: Apr. 17, 2015

(87) PCT Pub. No.: WO2014/178064
PCT Pub. Date: Nov. 6, 2014

(65) Prior Publication Data
US 2016/0168080 A1    Jun. 16, 2016

(30) Foreign Application Priority Data

Apr. 3, 2013 (IN) .......................... 1290/MUM/2013

(51) Int. Cl.
C07C 57/02    (2006.01)
C07C 249/12    (2006.01)
C07C 249/08    (2006.01)

(52) U.S. Cl.
CPC .......... *C07C 249/12* (2013.01); *C07C 249/08* (2013.01)

(58) Field of Classification Search
None
See application file for complete search history.

(56) References Cited

U.S. PATENT DOCUMENTS 4,081,551 A * 3/1978 Welle ............................ 514/523
4,085,225 A   4/1978 Welle et al.
6,433,225 B1  8/2002 Chitturi et al.

FOREIGN PATENT DOCUMENTS

CN    1079733 A  * 12/1993
CN    101654419 A * 2/2010

OTHER PUBLICATIONS

Machine transllation for CN 1079733.*
Machine transllation for CN 101654419 A.*
Shawn et al., "Efficient synthesis of chiral phenethylamines; preparation, asymmetric hydrogenation, and mild deprotection of ene-trifluoroacetamides" Tetrahedron Letters, vol. 47 (2006), pp. 6409-6412 p. 6410.

* cited by examiner

*Primary Examiner* — Sudhakar Katakam
*Assistant Examiner* — Ana Z Muresan
(74) *Attorney, Agent, or Firm* — Prakash Nama; Global IP Services, PLLC

(57) ABSTRACT

The present invention relates to an industrially feasible and economically viable process for the preparation of fluvoxamine maleate of formula I.

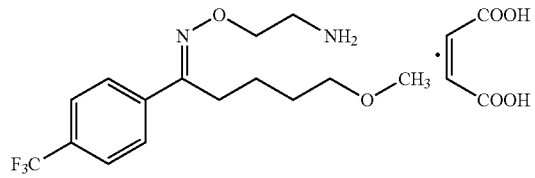

Formula I

5 Claims, No Drawings

PROCESS FOR THE PREPARATION OF FLUVOXAMINE MALEATE

FIELD OF THE INVENTION

The present invention relates to an improved and industrially applicable process for the preparation of fluvoxamine maleate of formula I,

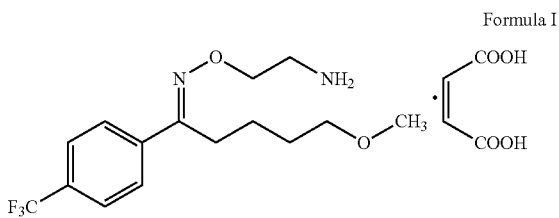

Formula I

BACKGROUND OF THE INVENTION

Fluvoxamine or (E)-5-methoxy-1-[4-(trifluoromethyl)phenyl]pentan-1-one-O-2-aminoethyl oxime is an antidepressant which functions as a selective serotonin reuptake inhibitor (SSRI). Fluvoxamine is used for the treatment of major depressive disorder (MDD), obsessive compulsive disorder (OCD), and anxiety disorders such as panic disorder and post-traumatic stress disorder (PTSD). Fluvoxamine CR (controlled release) is approved to treat social anxiety disorder.

Fluvoxamine maleate and compounds were first disclosed in U.S. Pat. No. 4,085,225. According to said patent, Fluvoxamine maleate prepared by alkylation reaction of 5-methoxy-4'-trifluoromethylvalerophenone oxime, compound of formula III with 2-chloroethylamine hydrochloride in dimethylformamide in the presence of a base such as potassium hydroxide powder for two days at 25° C.

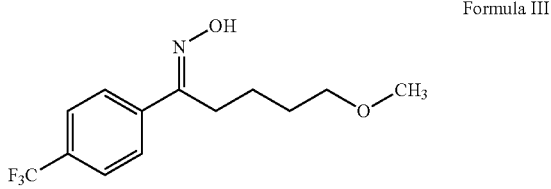 [SMILES: COCCCC/C(=N\O)c1ccc(C(F)(F)F)cc1]

Formula III

Subsequently the solvent is removed under vacuum then the residue is acidified and extracted with ether to remove the unreacted oxime followed by basification. The obtained fluvoxamine base in ether extract is washed with sodium bicarbonate solution. The fluvoxamine base is then treated with maleic acid in absolute ethanol and the residue obtained by concentration under vacuum is recrystallized from acetonitrile to obtain fluvoxamine maleate. The process is very much tedious, time consuming as it requires two days for the reaction completion. Operations like removal of dimethylformamide, ether, ethanol makes process cumbersome at plant level. Requirement of various solvents lead the process to be non-eco-friendly. Moreover the patent is silent about yield and purity of the product.

In an alternate route described in U.S. Pat. No. 4,085,225, the mine of formula III is converted to formula I in a five step process i.e. alkylation of formula III with ethylene oxide. The reaction solvent is ethanol in which lithium is already dissolved. The reaction further involves addition of acetic acid to give the hydroxyethyl compound of formula A as oil. The compound of formula A is purified chromatographically over the silica gel, which is converted to a mesylate compound of formula B by treating with methanesulfonyl chloride and triethylamine at −5 to 0° C., then aminated with ammonia in methanol at 100° C. using autoclave for 16 hours followed by removal of methanol and extraction in ether to give fluvoxamine base.

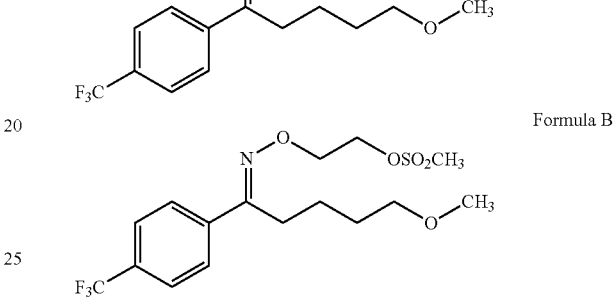

The base is then converted to the maleate salt formula I, which is finally purified by recrystallization from acetonitrile.

There are lots of disadvantages in like more unit operations, use of various solvents and handling of ethylene oxide which is also known for its carcinogen effect. More unit operations lead to long occupancy of reactors in the plant as well as man power, high energy consumption and require bigger plant. These all parameters make the process commercially unviable as well as environmentally non-feasible. Further, purification of the compound of formula A requires cumbersome technique i.e chromatography over silica gel as well as lengthy work-up procedure in U.S. Pat. No. 4,085,225 requires complete removal of organic solvents at various stages.

U.S. Pat. No. 6,433,225 discloses the process for preparing fluvoxamine maleate, prepared by alkylating 5-methoxy-4'-trifluoromethylvalerophenone oxime compound of formula III with 2-chloroethylamine hydrochloride in toluene and PEG-400 (polyethyleneglycol-400) as facilitator in the presence of a base potassium hydroxide powder at 30-35°C. to obtain fluvoxamine base in toluene layer is then treated with maleic acid in water. The precipitated fluvoxamine maleate is filtered and washed with toluene and dried. The obtained dried cake recrystallized with water to get fluvoxamine maleate. The process disclosed in the patent is silent about actual purity of the product. As per our scientist's observation alkylation reaction at the temperature of 30-35° C. may lead to non completion of reaction and results lower yield. Additional step of purification may further lead to loss of yield.

Thus, present invention fulfills the need of the art and provides an improved and industrially applicable process for preparation of fluvoxamine maleate, which provides fluvoxamine maleate in high purity and overall good yield.

OBJECTIVE OF THE INVENTION

The principal objective of the present invention is to provide an efficient and industrially advantageous process for preparation of fluvoxamine maleate.

Another prime objective of the invention is to provide an environment friendly process for the preparation of fluvoxamine maleate.

Another leading objective of the invention is to provide an efficient, improved and industrially advantageous process for preparation of fluvoxamine maleate which is conveniently applicable to industrial scale and avoiding use of various solvents.

Yet silent objective of the present invention is to provide a process for the preparation of fluvoxamine maleate wherein oxime formation is performed using sodium carbonate granules.

Yet additional objective of the present invention is to provide a process for the preparation of fluvoxamine maleate wherein oxime formation is in ratio of 95% syn isomer and 5% anti isomer by maintaining the reaction at 45-50'C.

Further one more objective of the present invention is to provide a process for the preparation of fluvoxamine maleate wherein alkylation reaction is performed at 40-45° C.

Yet supplementary objective of the present invention is to provide a process for the isolation of 5-methoxy-1-[4-(trifluoromethyl)phenyl]pentan-1-one from (1 E)+(1 Z) of 1-N-hydroxy-5-methoxy-1-[4-(trifluoromethyl)phenyl]pentan-1-imine.

Yet foremost objective of the present invention is to provide a process the preparation of fluvoxamine maleate having high purity and good yield.

SUMMARY OF THE INVENTION

Accordingly, the present invention provides an improved process for the preparation of fluvoxamine maleate of formula I,

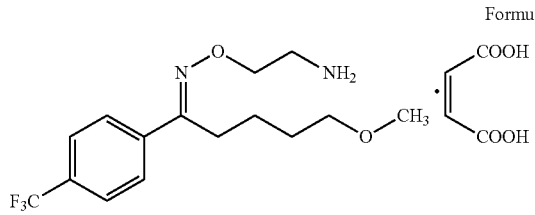

Formula I which proves to he efficient and industrially viable. The process comprises the steps of:

a). condensing the compound of formula II,

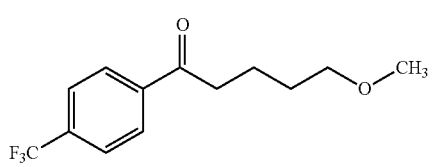

Formula II with hydroxylamine hydrochloride in the presence of sodium carbonate granules in suitable solvent to form a compound of formula III;

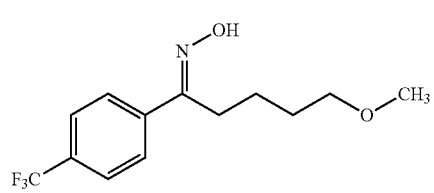

Formula III b). isolating compound of formula III;
c). treating compound of formula III with 2-chloroethylamine hydrochloride in the presence of base in suitable solvent at 40-45° C. to form compound of formula IV;

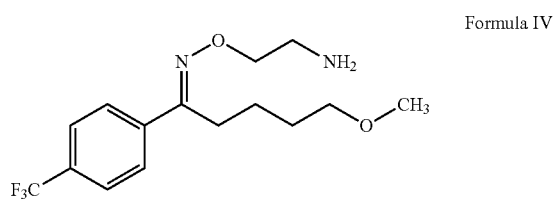 [SMILES: COCCCC/C(=N\OCCN)c1ccc(C(F)(F)F)cc1]

Formula IV d). extracting compound of formula IV with suitable solvent to form an organic layer;
e). treating organic layer of step d) with maleic acid;
f). isolating crude fluvoxamine maleate of formula I; and
g). optionally purifying fluvoxamine maleate of formula I.

Accordingly, the present invention provides a process for the preparation of compound of formula III, process comprises the step of treating compound of formula II with hydroxylamine hydrochloride in the presence of sodium carbonate granules in suitable solvent at temperature 45-50° C.

Accordingly, the present invention provides an improved process for the preparation of compound of formula I, process comprises the step of a) treating compound of formula III with 2-chloroethylamine hydrochloride in the presence of base in suitable solvent at 40-45° C. to form compound of formula IV; b) converting compound of formula IV into fluvoxamine maleate of formula I.

Accordingly, the present invention provides a process for the isolation of 5-methoxy-1-[4-(trifluoromethyl)phenyl]pentan-1-one of formula II from mixture of (1 E)+(1 Z) of 1-N-hydroxy-5-methoxy-1-[4-(trifluoromethyl)phenyl]pentan-1-imine of formula III by treating compound of formula III with aqueous hydrochloric acid.

Accordingly, the present invention provides an improved process for the preparation of pharmacopoeial grade fluvoxamine maleate.

DETAILED DESCRIPTION OF THE INVENTION

All ranges recited herein include the endpoints, including, those that recite a range "between" two values. Terms such as "about", "generally" and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

The present invention provides an improved and efficient process for the preparation of fluvoxamine maleate of formula I.

According to the embodiment of the invention provides an industrially viable process for preparation of fluvoxamine maleate starting from compound of formula II.

Stage 1:

The compound of formula II can be reacted with hydroxylamine hydrochloride in the presence of base in suitable solvent to form compound of formula III. Generally the reaction involves treatment of compound of formula II with hydroxylamine hydrochloride in the presence of base. Suitable base include organic base or inorganic base, wherein inorganic base includes alkali or alkaline metal hydroxides, carbonates, bicarbonates, alkoxides and organic base includes aliphatic amines, aromatic amines and ammonia and the like. Wherein base is preferably sodium hydroxide, potassium hydroxide, lithium hydroxide, sodium carbonate, potassium carbonate, lithium carbonate, sodium bicarbonate, potassium bicarbonate, lithium bicarbonate, triethylamine, diisopropylethylamine and the like; wherein base is more preferably sodium carbonate granules. Suitable solvents include, but are not limited to alcohol, ketone, nitrile, hydrocarbons and the like in any suitable proportion or mixtures thereof. The reaction mixture is heated at 40-120° C. for 1 to 24 hours, preferably at 40-70° C. for 10-15 hours, more preferably at 45-50° C. for 8-10 hours. The reaction completion is monitored by suitable chromatographic techniques such as high pressure liquid chromatography (HPLC) or thin layer chromatography (TLC). The compound of formula III can be isolated from the reaction mixture by suitable techniques such as extraction or filtration and the like. The process resulted in desired compound in high purity [98% syn (E-isomer) and 2% anti (Z-isomer)] and very good yield.

Particularly, compound of formula II is reacted with hydroxylamine hydrochloride in the presence of sodium carbonate granules in methanol solvent at temperature 45-50° C. for 8-10 hours to form compound of formula III. After completion of the reaction, the mixture is cooled to 25-30° C. and filtered under vacuum to remove unreacted inorganic matter. Methanol is distilled out under vacuum below 50° C. The obtained slurry is cooled to temperature 25-30° C. water is added into residue followed by addition of hexane for the extraction purpose and stirred for a while. Thus obtained two layers are separated. The organic layer is cooled to 0 to −20° C., preferably −5 to −10° C. and stirred for 30-40 minutes. The solid obtained is filtered and dried to get the compound of formula III.

The main advantage of the present invention is to make the process plant friendly and industrially viable in terms of yield and operations. Furthermore the present invention is advantageous as it resulted in good yield by inventing favorable parameters which can increase the yield and isolation of having very high ratio of desired E-isomer i.e syn-isomer of compound of formula III than z-isomer i.e anti-isomer of compound of formula III, preferably more than 98% syn (E-isomer). The present invention delivers more pure compound of formula III as compared to prior art processes. Using sodium carbonate in its granule form gives yield and purity wise extraordinary results at temperature 45-50° C. As per the observation by the scientists of the present invention that particle size of the sodium carbonate is the key parameter to get good yield and high purity. Moreover that the temperature below 45° C. and more than 50° C. resulted in comparatively low yield and purity: hence in this way the present invention is ameliorating one of the major drawback of the prior art processes.

Stage 2:

The compound of formula III can be reacted with 2-chloroethylamine hydrochloride in the presence of base in suitable solvent to form compound of formula IV. Generally the reaction involves condensation of compound of formula III with 2-chloroethylamine hydrochloride in the presence of base. Suitable base include organic base or inorganic base, wherein inorganic base includes alkali or alkaline metal hydroxides, carbonates, bicarbonates, alkoxides and organic base includes aliphatic amines, aromatic amines and ammonia and the like. Wherein base is preferably sodium hydroxide, potassium hydroxide, lithium hydroxide, sodium carbonate, potassium carbonate, lithium carbonate, sodium bicarbonate, potassium bicarbonate, lithium bicarbonate, triethylamine, diisopropylethylamine and the like; wherein base is more preferably potassium hydroxide. Suitable solvents include, but are not limited to polar aprotic solvent and the like; such as dimethylformamide (DMF), dimethylsulphoxide (DMSO), hexamethylphosphoramide (HMPA) in any suitable proportion or mixtures thereof. The reaction mixture is heated at 35-120° C. for 1 to 24 hours, preferably at 40-45° C. for 1-2 hours. After completion of the reaction and quenching with water, the product is extracted with solvent include hydrocarbons such as toluene and xylene. The compound of formula IV i.e fluvoxamine free base is being formed at this stage. Later the organic layer is reacted with maleic acid dissolved in water. The mixture stirred for 10-15 hours at temperature 20-70° C., preferably 2-3 hours at temperature 25-30° C. The reaction mixture cooled to 0-5° C. after maintaining 2-3 hours at temperature 25-30° C. The process resulted in desired compound of formula I.

Furthermore the present invention is advantageous as it resulted in high purity and yield by inventing and identifying favorable parameters which can decrease the formation of impurities. The scientists of the present invention observed that alkylation reaction at temperature 50-55° C. or higher temperature and at 40-45° C. for longer time is in favor to form high amount of impurities as structured below.

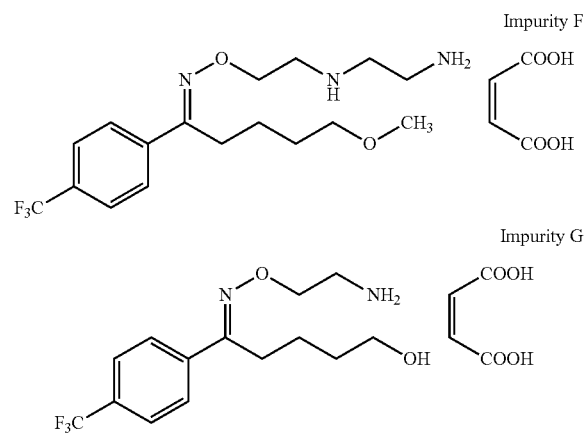

The present invention delivers more pure compound of formula IV as compared to prior art processes when the reaction performed at 40-45° C. for limited time gives best result in terms of purity as well as higher yield; hence in this way the present invention is ameliorating another major drawback of the prior art processes. The process becomes economically cost effective. The compound of formula I obtained by the present invention have purity more than 90%, preferably more than 95%, more preferably greater than 98%.

Stage 3:

Generally the reaction involves treatment of compound of formula I i.e fluvoxamine maleate crude with hot water to get pure fluvoxamine maleate. The reaction can be performed in water, wherein temperature of water is between 40-45° C. and stirred for 5-30 minutes; preferably 5-10 minutes. The reaction is then cooled to 25° C. and further addition of small amount of hydrocarbon solvent and stirred for a while followed by filtering, washing, and drying to get pure fluvoxamine maleate.

The main advantage of purification step is to reduce the impurities like impurity F, impurity G and formed process unknown impurities at 40-45° C.; purification at 40-45° C. is required because at lower temperature product is not soluble and foreign particles has to be removed. The addition of small amount of toluene is important to reduce formed unknown impurities. Upon increasing the temperature higher than 45° C. more impurities are formed. Hence the parameters set for the purification in present invention make the product pharmacopoeially acceptable worldwide.

According to another embodiment of the invention provides a process for the isolation of 5-methoxy-1-[4-(trifluoromethyl)phenyl]pentan-1-one of formula II from mixture of (1 E)+(1 Z) isomers of 1-N-hydroxy-5-methoxy-1-[4-(trifluoromethyl)phenyl]pentan-1-imine of formula III of stage-1 filtrate by treating compound of formula III with aqueous hydrochloric acid.

Particularly, the organic residue of (1 E)+(1 Z) isomers of 1-N-hydroxy-5-methoxy-1-[4-(trifluoromethyl)phenyl]pentan-1-imine of formula III of stage-1 hexane filtrate is treated with conc. HCl at temperature at about 50-80° C. for 1-24 hours, preferably 65-75° C. for 13-14 hours. The reaction mixture is cooled to 25-30° C., hexane is added into the reaction mixture and stirred for a while. Then organic layer is separated and treated with sodium bicarbonate solution. Further separation of layer followed by addition of water and stirred the reaction mixture at temperature 30-35° C. The mass is treated with activated charcoal and filtered. The filtrate is cooled to 0 to −5° C. to get the recovered 5-methoxy-1-[4-(trifluoromethyl)phenyl]pentan-1-one of formula II and recycled in subsequent batches.

The invention is further defined by reference to the following examples describing in detail by the preparation of the compounds of the invention. It will be apparent to those skilled in the art that many modifications, both to materials and methods, may be practiced without departing from the scope of the invention.

EXAMPLES

Stage-1: Preparation of (1 E)-N-hydroxy-5-methoxy-1-(4-trifluoromethyl phenyl)pentan-1-imine Formula III To a stirred solution of 5-methoxy-1-(4-trifluoromethyl-phenyl)pentan-1one (150 gm) in methanol (750 ml), sodium carbonate (granule) (72 gm) and hydroxylamine hydrochloride (59.64 gm) were added at temperature 25-30° C. The reaction mass was heated 45-50° C. for 10-15 minutes followed by maintaining the reaction mass at temperature 45-50° C. for 8-9 hours under stirring. The reaction mass was cooled to 25-30° C. and filtered under vacuum to remove unreacted inorganic matter, then distilled out the methanol completely from the collected filtrate under vacuum at temperature below 50° C. The obtained slurry was cooled to 25-30° C. and water (300 ml) was added into the residue followed by the addition of hexane (300×2 ml) and stirred for 30 minutes. The layers were separated. The collected organic layer was stirred for 5-10 minutes at temperature 25-30° C. followed by cooling the mass at temperature −5° C. to −10° C., stirred for 30-40 minutes and filtered at the same temperature. The product was suck dried at −5 to −10° C. and further in vacuum at 25-30° C. for 2-3 hours to give 138-142 gm of title compound. HPLC purity: >98.5%

Stage-2: Preparation of Crude Fluvoxamine Maleate Formula I

To a prepared solution of dimethyl sulphoxide (575 ml), potassium hydroxide flakes (114.64 gm) and water (69 ml), stage-1 (115 gm) was added at temperature 40-45° C. The reaction mixture was stirred to get clear solution followed by adding 2-chloroethylamine hydrochloride (8636 gm) drop wise into the reaction mixture at temperature 40-45° C. and maintained for 1-2 hour. Water (1150 ml) was added in to the reaction mixture at temperature 25-30° C. and stirred for 20-25 minutes. Then toluene (575 ml×2) was added and stirred for 30 minutes and preceded for separation of layers followed by washing the toluene layer with water (1150×5 ml). The solution of maleic acid (48.47 gm) dissolved in water (98 ml) was added into above obtained toluene layer and stirred at temperature 25-30° C. for 2-3 hours. The reaction mixture was cooled to 0-5° C. and maintained for 30-40 minutes at the same temperature. The obtained material was washed with toluene, filtered and such dried. The wet cake was then added hexane (600 ml) and stirred for 30 minutes at temperature 25-30° C., filtered, washed with hexane and dried to get 161 gm of title compound. HPLC purity: >98.5%

Stage-3: Preparation of Pure Fluvoxamine Maleate Formula I

In to the reaction assembly, water (600 ml) was added and heated to 40-45° C. Stage-2 (150 gm) was added into the hot water under stirring. The reaction mixture was stirred for 5-10 minutes, filtered and cooled to 25° C. Toluene (68 ml) was added into the reaction mixture at temperature 25° C. and stirred for 30 minutes. Filtered the solid, washed with 10-15° C. chilled water and dried to get the pure 127.5 gm fluvoxamine maleate. HPLC purity: >99.8%

Process for isolation of 5-methoxy-1-[4-(trifluoromethyl) phenyl]pentan-1-one Formula II To a solution of conc. HCl (600 ml) and water (160 organic residue (250 gm) of (1 E)+(1 Z) of 1-N-hydroxy-5-methoxy-1-[4trifluoromethyl)phenyl]pentan-1-imine and traces of 5-methoxy-1-[4-(trifluoromethyl)phenyl]pentan-1-one (obtained after hexane recovery from stage-1 filtrate) was added at temperature 25-30° C. under stirring. The reaction mixture was heated to 67-75° C. and maintained for 13-14 hours followed by cooling the reaction mixture at temperature 25-30° C. Then after hexane (500×2 ml) was added into the reaction mixture and stirred for 15 minutes at 25-30° C. The organic layers were separated and sodium bicarbonate solution (25 gm sodium bicarbonate dissolved in 250 ml water) was added into the hexane layer and stirred for 15 minutes. The layers were separated and water (250 ml) was added into hexane layer and stirred for 15 minutes at temperature 25-30° C. Further the layers were separated and hexane layer was added activated charcoal (12.5 gm) and stirred for 20-30 minutes at temperature 30-35° C. The reaction mixture was filtered and stirred for 5-10 minutes at 25-30° C. followed by cooling at 0 to −5° C. and stirred for 30-40 minutes at 0 to −5° C. The reaction mixture was filtered and dried to get 150 to 175 gm of title compound. HPLC purity: >99%.

We claim:

1. An improved process for the preparation of fluvoxamine maleate of formula I,

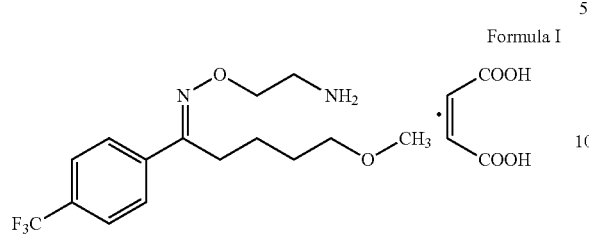
Formula I wherein the improvements comprises the steps of:
a). condensing the compound of formula II,

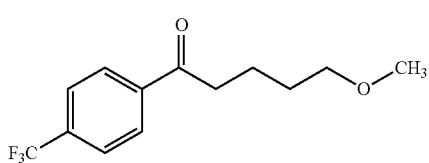
Formula II with hydroxylamine hydrochloride in the presence of sodium carbonate granules at temperature 45-50° C. in suitable solvent to form a compound of formula III, wherein the compound of formula III comprises a mixture of (1E)+(1Z) isomers of 1-N-hydroxy-5-methoxy-1-[4(trifluoromethyl)phenyl]pentan-1-imine, and wherein the mixture of (1E)+(1Z) isomers of 1-N-hydroxy-5-methoxy-1-[4(trifluoromethyl)phenyl]pentan-1-imine comprises 98% of E-isomer and 2% of Z-isomer;

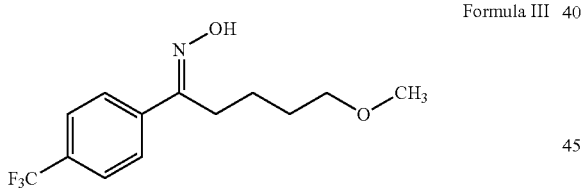
Formula III b). isolating compound of formula III;

c). treating compound of formula III with 2-chloroethyl-amine hydrochloride in the presence of base in suitable solvent at 40-45° C. to form compound of formula IV;

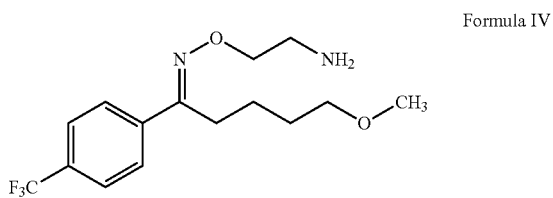 [SMILES: COCCCC/C(=N\OCCN)c1ccc(C(F)(F)F)cc1]
Formula IV d). extracting compound of formula IV with suitable solvent to form an organic layer;
e). treating organic layer of step d) with maleic acid;
f). isolating crude fluvoxamine maleate of formula I; and
g). optionally purifying fluvoxamine maleate of formula I.

2. The process according to claim 1, wherein in step a), said suitable solvent is selected from the group consisting of alcohol, ketone, nitrile, and hydrocarbons in any suitable proportion or mixtures thereof;
in step c), said base is selected from the group consisting of sodium hydroxide, potassium hydroxide, lithium hydroxide, sodium carbonate, potassium carbonate, lithium carbonate, sodium bicarbonate, potassium bicarbonate, lithium bicarbonate, triethylamine and diisopropylethyamine;
in step c), said solvent is selected from the group consisting of dimethylformamide (DMF), dimethylsulphoxide (DMSO) and hexamethylphosphoramide (HMPA) in any suitable proportion or mixtures thereof; and
in step d) said suitable solvent is selected from the group consisting of toluene and xylene.

3. A process for the isolation of 5-methoxy-1-[4-(trifluoromethyl)phenyl]pentan-1-one of formula II from mixture of (1E)+(1Z) of 1-N-hydroxy-5-methoxy-1-[4-(trifluoromethyl) phenyl]pentan-1-imine of formula III by treating compound of formula III with aqueous hydrochloric acid, wherein the mixture of (1E)+(1Z) of 1-N-hydroxy-5-methoxy-1-[4-(trifluoromethyl) phenyl]pentan-1-imine of formula III comprises 98% of E-isomer and 2% of Z-isomer.

4. The process according to claim 3, wherein the reaction is performed at temperature 65-75°C.

5. The process according to claim 1, wherein in step a), said suitable solvent is methanol.

* * * * *